United States Patent [19]

Roth et al.

[11] 4,229,453
[45] Oct. 21, 1980

[54] SUBSTITUTED 5,6-DIMETHYLPYRROLO[2,3-d]PYRIMIDINE COMPOUNDS, THEIR PRODUCTION AND THEIR MEDICINAL USE

[75] Inventors: Hermann J. Roth, Bad Honnef; Kurt Eger, Bonn-Endenich; Sedika Issa, Leverkusen; Haireddin Jacobi, Leichlingen, all of Fed. Rep. of Germany

[73] Assignee: Bayer Aktiengesellschaft, Leverkusen, Fed. Rep. of Germany

[21] Appl. No.: 28,028

[22] Filed: Apr. 6, 1979

[30] Foreign Application Priority Data

Apr. 27, 1978 [DE] Fed. Rep. of Germany ....... 2818676

[51] Int. Cl.$^2$ .................... A61K 31/495; C07D 487/04
[52] U.S. Cl. ..................................... 424/251; 544/280; 260/326.26
[58] Field of Search .......................... 544/280; 424/251

[56] References Cited

U.S. PATENT DOCUMENTS

| 2,759,949 | 8/1956 | Hitchings et al. | 544/262 |
| 3,187,006 | 6/1965 | Druey et al. | 544/262 |
| 3,296,261 | 1/1967 | Partyka | 544/280 |

FOREIGN PATENT DOCUMENTS 1481024  9/1962  France ...................................... 544/280

*Primary Examiner*—Donald G. Daus
*Assistant Examiner*—James H. Turnipseed

*Attorney, Agent, or Firm*—Sprung, Felfe, Horn, Lynch & Kramer

[57] ABSTRACT

The invention includes 5,6-dimethylpyrrolo [2,3-d]-pyrimidines (and method for their manufacture) of the formula

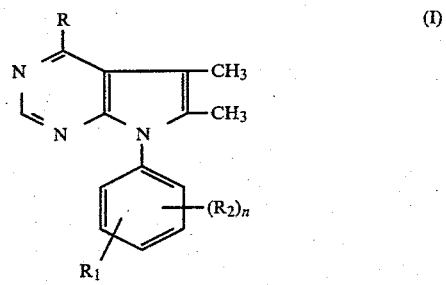

(I)

or an acid-addition salt thereof, in which
  R is amino or hydroxy,
  $R_1$ is halogen, nitro, $C_1$—$C_6$ alkyl or alkoxy or $CF_3$ and, where R is hydroxy, is also hydrogen,
  $R_2$ is hydrogen, halogen or $C_1$—$C_6$-alkyl or alkoxy, and
  n is 1 or 2.

Also included in the invention are pharmaceutical compositions containing said pyrrolo [2,3-d]-pyrimidines and the use of said compounds and compositions for treating CNS illnesses or inflammations.

13 Claims, No Drawings

SUBSTITUTED 5,6-DIMETHYLPYRROLO[2,3-d]PYRIMIDINE COMPOUNDS, THEIR PRODUCTION AND THEIR MEDICINAL USE

The present invention relates to certain new 5,6-dimethylpyrrolo[2,3-d]pyrimidines, to a process for their production and to their use as antiphlogistic agents and as agents for treatment of the central nervous system.

Some pyrrolo[2,3-d]pyrimidine derivatives are already known as biologically active compounds. Thus, derivatives are known which display a cytotoxic activity (J. A. MONTGOMERY et al., J. Med. Chem. 10 (1967), 665), and an antibiotic activity of other derivatives is described (J. F. GERSTER et al., J. Med. Chem. 10 (1967), 326). The preparation of similar pyrrolo[2,3-d]pyrimidines is likewise described (H. J. Roth et al., Arch. Pharmaz., 308, (1975), 252–258).

However, this class of compound has not yet found use in medicine.

According to the present invention we provide compounds which are 5,6-dimethylpyrrolo[2,3-d]pyrimidines of the general formula

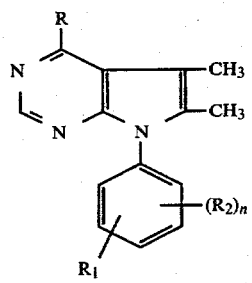

(I)

or an acid addition salt thereof in which

R denotes an amino or hydroxyl group, preferably an amino group, $R_1$ denotes a halogen atom, a nitro group, a $C_1$ to $C_6$ alkyl or alkoxy group or the trifluoromethyl group, and in the case where R is a hydroxyl group, also denotes a hydrogen atom, $R_2$ in each case denotes a hydrogen atom, a halogen atom or a $C_1$ to $C_6$ alkyl or alkoxy group and n is 1 or 2.

The present invention further provides a process for the production of compound of formula (I), in which a pyrrole derivative of the general formula

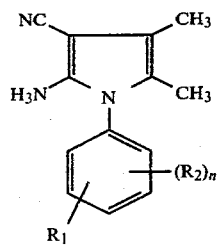

(II)

in which $R_1$, $R_2$ and n have the meaning indicated above, is reacted with a compound of the general formula

(III)

in which R denotes an amino or hydroxyl group, in the presence of formic acid and, optionally in the presence of inert organic solvents, at elevated temperature.

In the case where only formic acid (R=OH) is employed, compounds of the formula (I) in which R denotes a hydroxyl group are obtained, and in the case where an excess of formamide is employed in addition to formic acid, compounds of the formula (I) in which R denotes an amino group are obtained.

The compounds of the formula (I) according to the invention can be converted into acid addition salts, preferably physiologically acceptable acid addition salts, using suitable acids. The physiologically acceptable salts have the same advantageous properties as the free compounds.

In the general formulae (I) and (II): a halogen atom $R_1$ or $R_2$ preferably denotes the chlorine, bromine or fluorine atom; an alkyl group $R_1$ or $R_2$ preferably denotes a methyl, ethyl, propyl, isopropyl, butyl, isobutyl or tertiary butyl group, and the methyl group is particularly preferred; and an alkoxy group $R_1$ or $R_2$ preferably denotes the methoxy, ethoxy, propoxy or isopropoxy group, in particular the methoxy group.

The reaction according to the invention can be carried out in the presence or absence of diluents. Possible diluents are all the organic solvents in which the reactants dissolve and which do not themselves participate in the reaction. Dimethylformamide has proved particularly suitable.

The reaction temperatures can be varied within a substantial range. Preferably, the reaction is carried out at 50° to 160° C., preferably at 80° to 130° C.

In carrying out the reactions according to the invention, preferably an excess of formamide and/or formic acid of 0.06 to about 3 mols, more preferably of 1.5 to 2.5 mols, is employed per mol of the particular pyrrole derivative of the general formula (II). The formamide and formic acid can simultaneously serve as the solvent in this reaction.

Working up is carried out in a simple manner by standing the reaction solution in the cold, filtering off the precipitate which has separated out and recrystallising it from a suitable solvent.

Specific examples of new active compounds which may be mentioned are: 5,6-dimethyl-4-hydroxy-7-phenylpyrrolo-[2,3-d]pyrimidine, 4-amino-5,6-dimethyl-7-(α,α,α-trifluoro-m-tolyl)-pyrrolo[2,3-d]pyrimidine, 4-amino-5,6-dimethyl-7-(4-fluorophenyl)pyrrolo[2,3,-d]pyrimidine, 4-amino-5,6-dimethyl-7-(2,4,5-trichlorophenyl)pyrrolo[2,3-d]pyrimidine, 4-amino-5,6-dimethyl-7-(p-tolyl)pyrrolo[2,3-d]pyrimidine, 4-amino-5,6-dimethyl-7-(o-tolyl)pyrrolo[2,3-d]pyrimidine, 4-amino-5,6-dimethyl-7-(4-chlorophenyl)pyrrolo[2,3-d]pyrimidine, 4-amino-5,6-dimethyl-7-(4-methoxyphenyl)pyrrolo[2,3-d]pyrimidine, 4-amino-5,6-dimethyl-7-(2-methoxyphenyl)pyrrolo[2,3-d]pyrimidine, 4-amino-5,6-dimethyl-7-(4-bromophenyl)pyrrolo[2,3-d]pyrimidine, 4-amino-5,6-dimethyl-7-(2-bromophenyl)pyrrolo[2,3-d]pyrimidine, 4-amino-5,6-dimethyl-7-(4-nitrophenyl)-pyrrolo[2,3-d]pyrimidine, 4-amino-5,6-dimethyl-7-(3,4-dichlorophenyl)pyrrolo[2,3-d]pyrimidine and 4-amino-5,6-dimethyl-7-(3-chlorophenyl)pyrrolo[2,3-d]pyrimidine.

Most of the pyrrole derivatives of the general formula (II) employed as strarting compounds are known (U.S. Pat. No. 3,836,541). They can be prepared from acetoin, the corresponding amine and malonic dinitrile in accordance with the equation which follows:

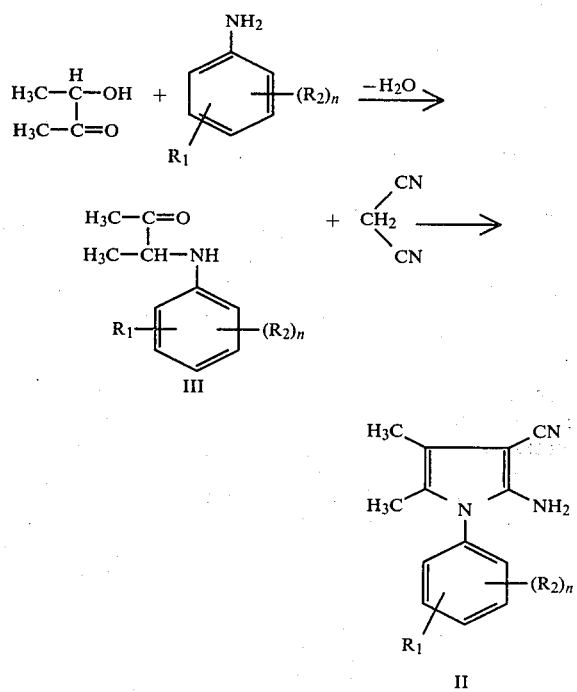

In this preparation, the condensation of acetoin with the corresponding amine is first carried out, in the presence of catalytic amounts of a strong acid, such as, for example, hydrochloric acid or p-toluenesulphonic acid, at the boil in a suitable solvent, such as, for example, benzene, water being separated off, to give the α-aminoketones of the general formula (III), which, however, are not isolated but immediately subjected to a further condensation reaction with malonic acid dinitrile under the influence of heat.

Working up is then generally carried out by evaporating off the solvent and recrystallising the residue from a suitable solvent.

Specific examples of 1-substituted 2-amino-3-cyano-4,5-dimethylpyrroles which may be mentioned are the following: 2-amino-1-(3-chlorophenyl)-3-cyano-4,5-dimethylpyrrole, 2-amino-1-(3,4-dichlorophenyl)-3-cyano-4,5-dimethylpyrrole, 2-amino-1-(2-bromophenyl)-3-cyano-4,5-dimethylpyrrole, 2-amino-1-(2-methoxyphenyl)-3-cyano-4,5-dimethylpyrrole, 2-amino-1-(2-tolyl)-3-cyano-4,5-dimethylpyrrole, 2-amino-1-(4-tolyl)-3-cyano-4,5-dimethylpyrrole, 2-amino-1-(3,4,5-trichlorophenyl)-3-cyano-4,5-dimethylpyrrole, 2-amino-1-(4-fluorophenyl)-3-cyano-4,5-dimethylpyrrole and 2-amino-1-(3-trifluoromethylphenyl)-2-amino-3-cyano-4,5-dimethylpyrrole.

Surprisingly, the compounds according to the invention have a number of advantageous pharmacological properties.

Thus, after oral administration, some of the compounds exhibit, in the hot plate test, a significant analgesic action which is more powerful than that of codeine or dextropropoxyphene (B. A. J. Janssen et al, J. Pharm. Pharmacol. 9, 381 (1957)).

As could be demonstrated by the balanced rod test, some of the compounds possess a sedative active component.

It could be shown, by the electric shock, the pentetrazole shock and the nicotine cramp tests, that some of the compounds according to the invention display a significant anticonvulsive activity. A muscle-relaxing action could be detected in some compounds by the traction test and the ptosis test (G. F. Holland et al, J. Med. Pharm. Chem. 3, 1 (1961)).

Finally, the compounds exhibited a surprisingly powerful antiphlogistic activity in the kaolin oedema test of rats' paws (Kemper, Z. ges. exp. Med. 131, 407, (1959)).

On the basis of these unexpected and diverse actions, the compounds according to the invention represent an advance in pharmacy.

As stated above, the invention also relates to the use in medicine of the compounds of the invention.

The present invention provides pharmaceutical compositions containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides pharmaceutical compositions containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents. e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the sual diulents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, bloodisotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The product of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously) rectally or locally, preferably orally or rectally. Preferred pharmaceutical compositions and medicaments are therefore those adapted for administration such as oral or rectal administration. Administration in the method of the invention is preferably oral or rectal administration. 5,6-Dimethyl[2,3-d]pyrimidines of the general formula (I) in which R denotes an amino or hydroxyl group,
$R_1$ denotes a fluorine, chlorine or bromine atom or a nitro, trifluoromethyl, methyl, ethyl, methoxy or ethoxy group,
$R_2$ denotes a hydrogen, fluorine, chlorine or bromine atom or a methoxy or methyl group and
n is 1 or 2, and acid addition salts thereof, especially physiologically acceptable acid addition salts, of these compounds are of particular interest.

The following Examples 1 to 14 illustrate the preparation of individual compounds of the invention and Example 15 illustrates the preparation of precursors.

EXAMPLE 1

4-Amino-7-(4-chlorophenyl)-5,6-dimethylpyrrolo[2,3-d]pyrimidine 15 g (0.06 mol) of 2-amino-1-(4-chlorophenyl)-3-cyano-4,5-dimethylpyrrole in 100 ml of formamide, 30 ml of dimethylformamide and 15 ml of concentrated formic acid are heated under reflux for 7 hours. The crystals which precipitate on cooling are washed with water and recrystallised from ethanolic potassium hydroxide solution. Melting point: 250° C., yield: 13 g (79% of theory).

$C_{14}H_{13}ClN_4$ (272.5) calculated: C 61.65%, H 4.7%, N 20.5%, Cl 13.0:, found: C 61.73%, H 4.78%, N 20.30%, Cl 13.9%.

EXAMPLE 2

4-Amino-7-(4-nitrophenyl)-5,6-dimethylpyrrolo[2,3-d]pyrimidine

The compound is formed from 0.03 mol of 1-(4-nitrophenyl)-2-amino-3-cyano-4,5-dimethylpyrrole, after boiling for 18 hours, analogously to the compound described in Example 1, Melting point 310° C. (dimethylformamide), yield: 5.6 g (64% of theory).

$C_{14}H_{13}N_5O_2$ (283) calculated: C 59.36%, H 4.59%, N 24.73%;

found: C 59.47%, H 4.84%, N 24.58%.

EXAMPLE 3

4-Amino-7-(4-methoxyphenyl)-5,6-dimethylpyrrolo[2,3-d]pyrimidine

The compound is obtained from 4.82 g (0.02 mol) of 1-(4-methoxyphenyl)-2-amino-3-cyano-4,5-dimetnylpyrrole in a reaction time of 7 hours, analogously to Example 1. Melting point: 225° C. (ethanolic KOH), yield: 4.5 g (85% of theory).

$C_{15}H_{16}N_4O$ (268) calculated: C 67.10%, H 5.90%, N 20.80%;

found: C 67.09%, H 5.11%, N 20.53%.

EXAMPLE 4

4-Amino-7-(4-bromophenyl)-5,6-dimethylpyrrolo[2,3-d]pyrimidine

The compound is obtained from 26 g (0.09 mol) of 1-(4-bromophenyl)-2-amino-3-cyano-3,4-dimethylpyrrole in a 7-hour reaction, analogously to Example 1. Melting point: 254° to 252° C. (ethanolic KOH), yield: 25 g (82.7% of theory).

$C_{14}H_{13}BrN_4$ (315.9) calculated: C 53.1%, H 4.11%, N 17.72%. Br 25.29%;

found: C 52.97%, H 4.15%, N 17.55%, Br 25.33%.

EXAMPLE 5

4-Amino-7-(2-bromophenyl)5,6-dimethylpyrrolo[2,3-d]pyrimidine

The compound is obtained from 1-(2-bromophenyl)-2-amino-3-cyano-4,5-dimethylpyrrole in a 7-hour reaction, analogously to Example 1. Melting point: 233° to 235° C. (ethanolic KOH), yield: 2.4 g (79% of theory).

$C_{14}H_{13}BrN_4$ (315.9) calculated: C 53.1%, H 4.11%, N 17.72%, Br 25.29%;

found: C 52.88%, H 4.12%, N 17.46%, Br 25.54%.

The following compounds were prepared analogously to Examples 1 to 5 described above:

EXAMPLE 6

4-Amino-7-(4tolyl)-5,6-dimethylpyrrolo[2,3-d]pyrimidine

Melting point: 225° C.

$C_{15}H_{16}N_4$ (252) calculated: C 71.40%, H 6.39%, N 22.21%;

found: C 71.37%, H 6.50%, N 22.13%.

EXAMPLE 7

4-Amino-7-(2-tolyl)-5,6-dimetnylpyrrolo[2,3-d]pyrimidine

Melting point: 195° C.

$C_{15}H_{14}N_4$ (252) calculated: C 71.40%, H 6.39%, N 22.21%.

found: C 71.34%, H 6.58%, N 22.04%.

EXAMPLE 8

4-Amino-7-(2-methoxyphenyl)-5,6-dimethylpyrrolo[2,3-d]pyrimidine

Melting point: 245° C.

$C_{15}H_{16}N_4O$ (268) calculated: C 67.5%, H 5.9%, N 20.8%;

found: C 66.78%, H 5.96%, N 20.66%.

EXAMPLE 9

4-Amino-7-(3-trifluoromethylphenyl)-5,6-dimethylpyrrolo[2,3-d]pyrimidine

Melting point: 230° C.

$C_{15}H_{13}F_3N_4$ (305) calculated: C 59.0%, H 4.26%, N 18.36%, F 16.27%;

found: C 58.44%, H 4.30%, N 18.06%, F 18.66%.

EXAMPLE 10

4-Amino-7-(4-fluorophenyl)5,6-dimethylpyrrolo[2,3-d]pyrimidine

Melting point: 232° C.

$C_{14}H_{13}FN_4$ (256) calculated: C 65.62%, H 5.07%, N 21.8%, F 7.41%;

found: C 65.54%, H 5,12%, N 21.4%, F 7.3%.

EXAMPLE 11

4-Amino-7-(2,4,5-trichlorophenyl)5,6-dimethylpyrrolo[2,3-d]pyrimidine

Melting point: 248° C.

$C_{14}H_{11}Cl_3N_4$ (341.5) calculated: C 49.26%, H 3.25%, N 16.39%, Cl 31.18%;

found: C 49.20%, H 3.30%, N 16.41%, Cl 31.09%.

EXAMPLE 12

4-Amino-7-(3,4-dichlorophenyl)-5,6-dimethylpyrrolo[2,3-d]pyrimidine

Melting point: 270° C.

$C_{14}H_{12}Cl_2N_4$ calculated: C 54.72%, H 3.90%, N 18.2%, Cl 23.15%;

found: C 54.68%, H 4.06%, N 18.08%, Cl 23.18%.

EXAMPLE 13

4-Amino-7-(3-chlorophenyl)-5,6-dimethylpyrrolo[2,3-d]pyrimidine

Melting point 210° C.

$C_{14}H_{13}ClN_4$ (272.5) calculated: C 61.65%, H 4.7%, N 20.50%, Cl 13.0%;

found: C 61.45%, H 4.9%, N 20.53%, Cl 13.12%.

EXAMPLE 14

5,6-Dimethyl-4-hydroxy-7-phenylpyrrolo[2,3-d]pyrimidine 6.2 g (0.03 mol) of 2-amino-3-cyano-4,5-dimethyl-1-phenylpyrrole in 60 ml of 85% strength formic acid are boiled under reflux for 12 hours. The crystals which precipitate on cooling are recrystallised from dimethylformamide.

Melting point: 295° C., yield: 4.2 g (64% of theory).

EXAMPLE 15

Some of the substituted pyrroles used as the starting material have not yet been described in the literature.

They can be prepared in a simple manner according to the following general instructions:

Equimolar amounts of acetoin and the appropriate amine (in the order of 5 to 15 g) are dissolved in 80 to 100 ml of benzene (3 drops of concentrated hydrochloric acid or 0.1 g of p-toluenesulphonic acid being added if necessary) and the solution is boiled, using a water separator, until the theoretical amount of water has been separated off. Equimolar amounts of malononitrile are added to this reaction solution, which is still warm (a little piperidine is added if necessary), and the mixture is boiled further until the required amount of water to be separated off is achieved. After evaporating off the solvent in vacuo, the residue is recrystallised from alcohol or dimethylformamide.

The following pyrroles can be prepared by this

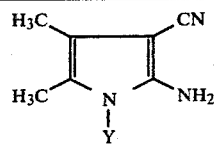

| Y | Melting point | Yield |
|---|---|---|
| 4-Br-phenyl | 167° C. | 89,6 % |
| 4-OCH₃-phenyl | 162–164° C. | 49% |
| 4-NO₂-phenyl | 207° C. | 74% |
| 4-Cl-phenyl | 164° C. | 73 % |
| phenyl | 135° C. | 65 % |
| 2-Br-phenyl | 135° C. | 21 % |
| 2-CH₃-phenyl | 125° C. | 36 % |
| 4-CH₃-phenyl | 163–165° C. | 34 % |
| 2-OCH₃-phenyl | 120° C. | 30 % |
| 3-Cl-phenyl | 158° C. | 21 % |
| 3,4-diCl-phenyl | 175° C. | 22 % |
| 4-F-phenyl | 115° C. | 22 % |
| 2,4,5-triCl-phenyl | 180° C. | 25 % |

The present invention also comprises pharmaceutically acceptable bioprecursors of the active compounds of the present invention.

For the purposes of this Specification the term 'pharmaceutically acceptable bioprecursor' of an active compound of the invention means a compound having a structural formula different from the active compound but which nonetheless, upon administration to an animal or human being is converted in the patient's body to the active compound.

It will be understood that the specification and examples are illustrative but not limitative of the present invention and that other embodiments within the spirit and scope of the invention will suggest themselves to those skilled in the art.

What is claimed is:

1. A 5,6-dimethylpyrrolo[2,3-d]pyrimidine compound of the formula

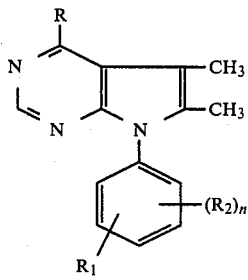

or a physiologically acceptable acid-addition salt thereof, in which

R denotes amino or hydroxyl,

R₁ denotes halogen, nitro,

C₁ to C₆ alkyl or trifluoromethyl, and in the case where R is hydroxyl, also denotes hydrogen, R₂ in each case denotes hydrogen, halogen or C₁ to C₆ alkyl or alkoxy and n is 1 or 2.

2. A compound according to claim 1, in which R denotes amino.

3. A compound according to claim 1, in which R₁ denotes fluorine, chlorine, bromine or nitro, trifluoromethyl, methyl, ethyl, methoxy or ethoxy, and R₂ denotes hydrogen, fluorine, chlorine or bromine or methoxy or methyl or a physiologically acceptable acid addition salt thereof.

4. A compound according to claim 1, which is 4-Amino-7-(2-bromophenyl)-5,6-dimethylpyrrolo[2,3-d]pyrimidine.

5. A compound according to claim 1, which is 4-Amino-7-(2-tolyl)-5,6-dimethylpyrrolo[2,3-d]pyrimidine.

6. A compound according to claim 1, which is 4-Amino-7-(2-methoxyphenyl)-5,6-dimethylpyrrolo-[2,3-d]pyrimidine.

7. A pharmaceutical composition containing as an active ingredient an effective antiphlogistic, sedative or anticonvulsive amount of a compound according to claim 1 in admixture with a solid or liquefied gaseous diluent or in admixture with a liquid diluent other than a solvent of a molecular weight less than 200 except in the presence of a surface-active agent.

8. A pharmaceutical composition containing as an active ingredient an effective antiphlogistic sedative or anticonvulsive amount of a compound according to claim 1 in the form of a sterile or physiologically isotonic aqueous solution.

9. A composition according to claim 7 or 8 containing from 0.5 to 95% by weight of the said active ingredient.

10. A medicament in dosage unit form comprising an effective antiphlogistic, sedative or anticonvulsive amount of a compound according to claim 1 together with an inert pharmaceutical carrier.

11. A medicament of claim 10 in the form of tablets, pills, dragees, capsules, ampoules, or suppositories.

12. A method of treating warm-blooded animals which comprises administering to the animals an effective antiphlogistic, sedative or anticonvulsive amount of an active compound according to claim 1 either alone or in admixture with a diluent or in the form of a medicament.

13. A method according to claim 12 in which the active compound is administered orally or rectally.

* * * * *